May 10, 1960 M. L. MEILLAND Plant Pat. 1,939
ROSE PLANT
Filed Feb. 16, 1959
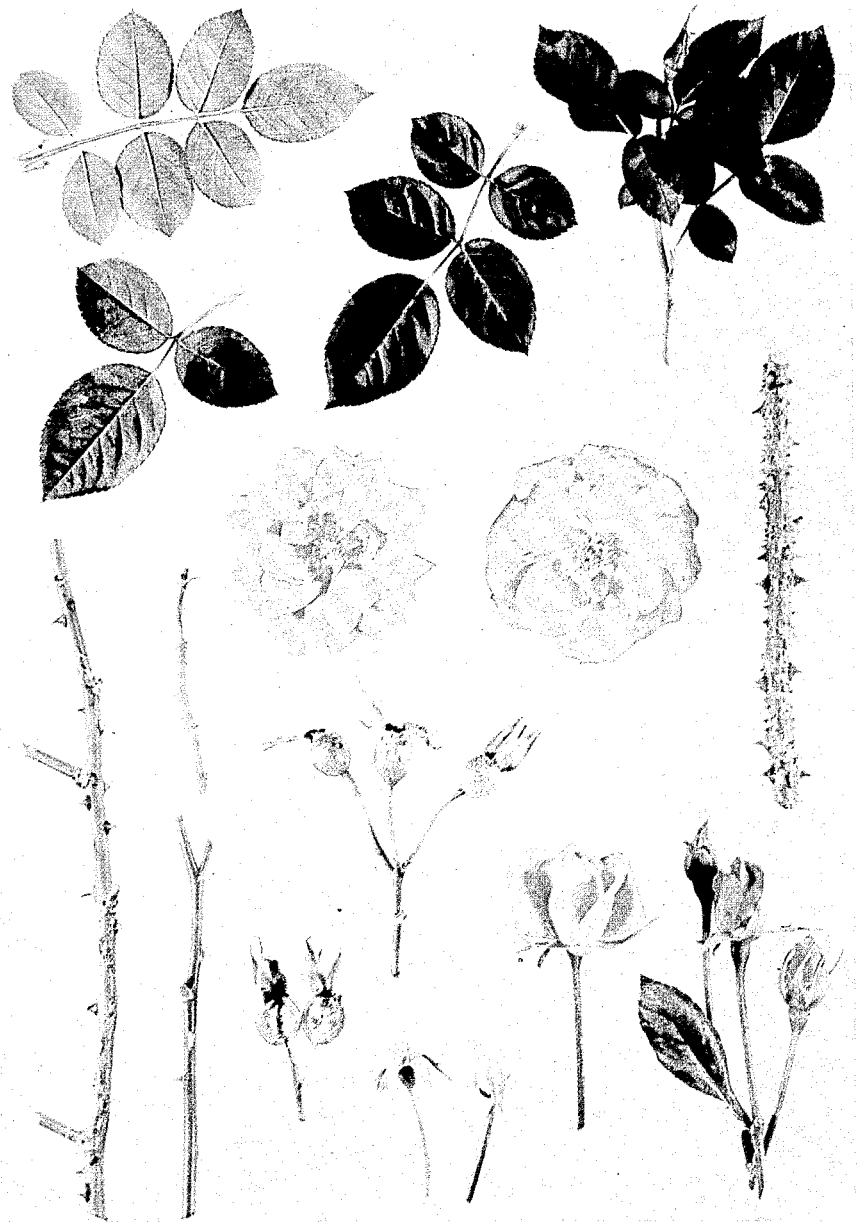
INVENTOR
Marie Louise Meilland
BY Robb & Robb
ATTORNEYS United States Patent Office Plant Pat. 1,939
Patented May 10, 1960

1,939

ROSE PLANT

Marie Louise Meilland, Cap d'Antibes, Alpes Maritimes, France, assignor to The Conard-Pyle Company, West Grove, Pa., a corporation of Pennsylvania Application February 16, 1959, Serial No. 793,657

Claims priority, application France July 24, 1958

1 Claim. (Cl. 47—61)

The present invention relates to a new and distinct variety of rose plant of the hybrid polyantha class, which was originated by me by crossing the variety "Moulin Rouge" (U.S. Plant Patent No. 1,298) with the variety "Fashion" (U.S. Plant Patent No. 789).

The primary objective of this breeding was to produce a new variety of rose plant combining the vigor and plant habit of the parent variety "Moulin Rouge" with the Coral-Peach general color tonality of the blooms and free-flowering habit of the parent variety "Fashion." This objective was fully achieved, along with other improvements, as evidenced by the following unique combination of characteristics which are outstanding in the new variety and which distinguish it from its parents as well as from all other varieties of which I am aware:

(1) A dense, bushy and well-balanced habit of growth;

(2) Attractive, dark green foliage;

(3) An excellent form and good substance of the blooms; and (4) A distinctive Claret Rose general color tonality of the flowers.

Asexual reproduction of the new variety by budding, as performed at West Grove, Pennsylvania, U.S.A. and also in France, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the Royal Horticultural Society, except where general color terms of ordinary dictionary significance are obvious:

Type: Hardy; bush; outdoor; seedling; for cut flowers and for garden decoration.

Class: Hybrid polyantha.

Breeding: Seedling.

*Seed parent.*—"Moulin Rouge."

*Pollen parent.*—"Fashion."

Propagation: Holds its distinguishing characteristics through succeeding propagations by budding.

*Flower*

Locality where grown and observed: West Grove, Pennsylvania, U.S.A.

Flowers borne: Several to stem; in regular, flat clusters; on stems of medium length and normal strength.

Quantity of bloom: Free, outdoors.

Continuity: Continuous.

Fragrance: From slight to moderate. Nature—tea.

Bud:

*Peduncle.*—Medium length; medium caliper; erect; rough; with medium number of red-brown hairs. Color—Scheele's Green, Plate 860/2.

*Before calyx breaks.*—Size—from small to medium. Form—pointed-ovoid; with a conspicuous neck; with foliaceous appendages on the surface of the bud; with slender, entire foliaceous parts extending beyond the tip of the bud equal to ¼ or more of its length.

*As calyx breaks.*—Color—Garnet Lake, Plate 828, with blackish shadings.

*As first petal opens.*—Size—medium. Form—medium length; ovoid. Color: outside—Claret Rose, Plate 021, irregularly blotched with Maroon, Plate 1030; inside—Delft Rose, Plate 020/1 at margin, shading to Geranium Lake, Plate 20/1.

*Opening.*—Opens up well.

Bloom:

*Size (when fully open).*—Medium; from 3 inches to 3½ inches.

*Petalage.*—Double; from 40 to 45 petals; arranged regularly.

*Form.*—Cupped and high-centered at first, but becoming flat; petals being at first loosely rolled outward, but becoming later at maturity very loosely rolled outward.

Petals: Thick; with inside velvety and outside satiny.

*Shape.*—Outer—round, with generally one shallow notch. Intermediate—round, with one or two notches. Inner—obovate; irregular.

This description of a newly opened flower was made from a rose grown outdoors in the month of September at West Grove, Pennsylvania, U.S.A.:

*Color.*—Outer petal: outside surface—Spinel Red, Plate 0023, washed irregularly with Spinel Red, Plate 0023/1, with point of attachment Pea Green, Plate 61/3; inside surface—Claret Rose, Plate 021/1, with point of attachment Chartreuse Green, Plate 663/2. Intermediate petal: outside surface—Spinel Red, Plate 0023/1, with point of attachment between Pea Green, Plate 61/2 and Pea Green, Plate 61/3; inside surface—Claret Rose, Plate 021/1, grading to Camellia Rose, Plate 622, with point of attachment Chartreuse Green, Plate 663/2. Inner petal: outside surface—Rose Madder, Plate 23/1, often with streaks of Spinel Red, Plate 0023/3 spreading from the base, with point of attachment Pea Green, Plate 61/3, veined with Pea Green, Plate 61/2; inside surface—Claret Rose, Plate 021/1, with point of attachment Chartreuse Green, Plate 663.

This description was made from a rose that was open for 3 days outdoors in the month of September at West Grove, Pennsylvania, U.S.A.:

*Color.*—Outer petal: outside surface—China Rose, Plate 024/1, grading to Rose Bengal, Plate 25/2 at base, with point of attachment Pea Green, Plate 61/3; inside surface—Rose Opal, Plate 022/1, grading to Spinel Pink, Plate 0625/1 at base, with point of attachment Chartreuse Green, Plate 663/3. Inner petal: outside surface—Rose Bengal, Plate 25/2, with point of attachment near Pea Green, Plate 61/3; inside surface—Rose Opal, Plate 021/1 at outer margin, with main body of petal Spinel Pink, Plate 0625/1, with tints of Rose Bengal, Plate 25/3 at base, with point of attachment Chartreuse Green, Plate 663/3.

*General color effect.*—Newly opened flower—Claret Rose, Plate 021/1. 3-days open—Spinel Pink, Plate 0625/1, with margins of petals Rose Opal, Plate 021/1.

*Behavior.*—Drop off cleanly.

*Flower longevity.*—On bush in garden—3 days in September. Cut roses grown outdoors and kept at livingroom temperatures—4 days in September.

*Reproductive organs*

Stamens: Many; arranged irregularly about pistils.
Filaments: Many; most with anthers; medium length. Color—Sulphur Yellow, Plate 1/1.
Anthers: All open at once; medium size; occasionally an anther fused with a petaloid. Color—Indian Yellow, Plate 6.
Pollen: From moderate abundance to abundant. Color—gold.
Pistils: Medium number.
Styles: Uneven, medium length; medium caliper; bunched.
Stigma: Color—white.
Ovaries: All enclosed in receptacle.
Hips: Medium length; oblong; with inconspicuous neck; moderately rough; walls medium fleshy. Color—reddish.
Sepals: Permanent; medium length; straight.
Seeds: Many; medium size.

*Plant*

Foliage:

*Leaves.*—Compound of 3, 5 or 7 leaflets; normal abundance; medium size; moderately glossy.

*Leaflets.* — Shape — oval, with apex acuminate. Base—obtuse. Margin—simply serrate.

*Color.*—Mature: upper surface—Spinach Green, Plate 0960; under surface—Lavender Green, Plate 000761. Young: upper surface—Spinach Green, Plate 0960, overlaid with Maroon, Plate 1030; under surface—Fern Green, Plate 0862, partly overlaid with Oxblood Red, Plate 00823/3.

*Rachis (the supporting stem of the compound leaf).*—Medium caliper. Upper side—grooved; hairy. Under side—sparsely prickly.

*Stipules.*—Medium length; moderately wide; with points of medium length turning out at an angle of more than 45°.

*Disease resistance.*—Comparable to that of the average variety grown under the same cultural conditions at West Grove, Pennsylvania, U.S.A.

Growth:

*Habit.*—Bushy; much-branched.

*Growth.*—From free to vigorous.

*Canes.*—Medium caliper.

*Main stems.*—Bright. Color—Spinach Green, Plate 0960/2, with occasional blotches of Oxblood Red, Plate 00823. Prickles—several; color—Garnet Brown, Plate 00918. Hairs—none.

*Branches.*—Bright. Color—Spinach Green, Plate 0960/1. Prickles—several; color—Oxblood Red, Plate 00823/3. Hairs—none.

*New shoots.*—Bright. Color—Lettuce Green, Plate 861, overlaid with Oxblood Red, Plate 00823/2 where exposed to the sun. Prickles—several; color—Oxblood Red, Plate 00823. Hairs—none.

I claim:

A new and distinct variety of rose plant of the hybrid polyantha class, substantially as herein shown and described, characterized particularly as to novelty by the unique combination of a dense, bushy and well-balanced habit of growth, attractive dark green foliage, excellent form and good substance of the blooms, and a distinctive Claret Rose general color tonality of the flowers.

No references cited.